US00PP25961P2

(12) United States Plant Patent
Moen

(10) Patent No.: US PP25,961 P2
(45) Date of Patent: Sep. 29, 2015

(54) ***GERBERA* PLANT NAMED 'GARJASMINA IMP.'**

(50) Latin Name: *Gerbera hybrida*
Varietal Denomination: Garjasmina Imp.

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 37 days.

(21) Appl. No.: 13/999,239

(22) Filed: Jan. 31, 2014

(51) Int. Cl.
*A01H 5/02* (2006.01)

(52) U.S. Cl.
USPC ..... Plt./357

(58) Field of Classification Search
USPC ..... Plt./357
CPC ..... A01H 5/025; A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Gerbera* plant named 'Garjasmina Imp.', characterized by its compact, broadly upright and uniformly mounding plant habit; dense and bushy appearance; numerous inflorescences with red and red purple-colored ray florets arranged on upright and strong scapes; and good garden performance.

1 Drawing Sheet

Botanical designation: *Gerbera hybrida.*
Cultivar denomination: 'GARJASMINA IMP.'.

BACKGROUND OF THE INVENTION

The present invention relates to a new and distinct cultivar of *Gerbera* plant, botanically known as *Gerbera hybrida* and hereinafter referred to by the name 'Garjasmina Imp.'.

The new *Gerbera* plant is a product of a planned breeding program conducted by the Inventor in De Kwakel, The Netherlands. The objective of the breeding program is to create new compact *Gerbera* plants with numerous inflorescences, good garden performance, frost tolerance and attractive inflorescence coloration.

The new *Gerbera* plant is a naturally-occurring whole plant mutation of *Gerbera hybrida* 'Garjasmina', not patented. The new *Gerbera* plant was discovered and selected by the Inventor as a single flowering plant within a population of plants of 'Garjasmina' in a controlled greenhouse environment in De Kwakel, The Netherlands in April, 2012.

Asexual reproduction of the new *Gerbera* plant by cuttings and by tissue culture in a controlled environment in De Kwakel, The Netherlands since September, 2012 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garjasmina Imp.'. These characteristics in combination distinguish 'Garjasmina Imp.' as a new and distinct *Gerbera* plant:

1. Compact, broadly upright and uniformly mounding plant habit.
2. Dense and bushy appearance.
3. Numerous inflorescences with red and red purple-colored ray florets.
4. Upright and strong scapes.
5. Good garden performance, relatively tolerant to rain, wind and low temperatures.

Plants of the new *Gerbera* differ from plants of the parent, 'Garjasmina', in the following characteristics:

1. Plants of the new *Gerbera* are more vigorous than plants of 'Garjasmina'.
2. Plants of the new *Gerbera* have larger leaves than plants of 'Garjasmina'.
3. Plants of the new *Gerbera* have larger inflorescences than plants of 'Garjasmina'.

Plants of the new *Gerbera* can be compared to plants of the *Gerbera hybrida* 'Garlisa', disclosed in U.S. Plant Pat. No. 22,804. Plants of the new *Gerbera* differ from plants of 'Garlisa' in the following characteristics:

1. Plants of the new *Gerbera* have narrower leaves than plants of 'Garlisa'.
2. Plants of the new *Gerbera* and 'Garlisa' differ in ray floret shape as plants of 'Garlisa' have narrowly elliptic-shaped ray florets.
3. Plants of the new *Gerbera* and 'Garlisa' differ slightly in ray floret color as plants of 'Garlisa' have red purple-colored ray florets.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garjasmina Imp.' grown in a container.

DETAILED BOTANICAL DESCRIPTION

The aforementioned photograph and following observations and measurements describe plants grown during the autumn and early winter in 15-cm containers in a glass-covered greenhouse in De Kwakel, The Netherlands and under cultural practices typical of commercial *Gerbera* production. During the production of the plants, day temperatures ranged from 10° C. to 16° C. and night temperatures averaged 10° C. Rooted young tissue-cultured plants were five months old when the photograph and the description were taken. In the following description, color references are made to The Royal Horticultural Society Colour Chart, 2007 edition, except where general terms of ordinary dictionary significance are used.

Botanical classification: *Gerbera hybrida* 'Garjasmina Imp.'.

Parentage: Naturally-occurring whole plant mutation of *Gerbera hybrida* 'Garjasmina', not patented.

Propagation:

*Type*.—By tissue culture.

*Time to initiate roots, summer and winter*.—About 2.5 to 3 weeks at temperatures of 20° C.

*Time to produce a rooted young plant, summer and winter*.—About five to six weeks at temperatures of 20° C. to 26° C.

*Root description*.—Fibrous; white in color.

Plant description:

*Appearance*.—Herbaceous perennials that are typically grown as container or garden plants; compact and uniformly mounding plant habit, broadly upright and roughly globular in shape; numerous leaves arranged in basal rosettes and outwardly arching; dense and bushy habit; inflorescences held above the foliar plane on erect and strong basal scapes; moderately vigorous growth habit.

*Plant height, soil level to top of foliar plane*.—About 25.4 cm.

*Plant height, soil level to top of inflorescences*.—About 44.5 cm.

*Plant width*.—About 50 cm.

Leaf description:

*Arrangement*.—Alternate, simple.

*Length*.—About 23.4 cm.

*Width*.—About 9.4 cm.

*Shape*.—Narrowly oblong; runcinate.

*Apex*.—Acute.

*Base*.—Acuminate.

*Margin*.—Coarsely and irregularly angulate; sinuses divergent; undulate.

*Texture, upper surface*.—Sparsely pubescent.

*Texture, lower surface*.—Densely tomentose.

*Venation pattern*.—Pinnate.

*Color*.—Developing leaves, upper surface: Darker than 143A. Developing leaves, lower surface: Close to 143A to 143B. Fully expanded leaves, upper surface: Close to N137A; venation, close to 144A. Fully expanded leaves, lower surface: Close to 147B; venation, close to 144A to 144B.

*Petioles*.—Length: About 6 cm. Diameter: About 4 mm. Texture, upper and lower surfaces: Moderately pubescent. Color, upper surface: Close to 144B tinged with close to 176D. Color, lower surface: Close to 144B tinged with close to 182D.

Inflorescence description:

*Appearance*.—Composite inflorescence form with oblanceolate-shaped ray florets; solitary inflorescences borne on upright and strong scapes above the foliar plane; ray and disc florets arranged acropetally on a capitulum.

*Fragrance*.—None detected.

*Flowering season*.—Plants begin flowering about three months after planting; under garden conditions in The Netherlands, plants flower from spring to late summer; plants can be flowered year-round in the greenhouse.

*Inflorescence longevity*.—Depending on the temperature, inflorescences last about two weeks on the plant; inflorescences not persistent.

*Quantity of inflorescences*.—Freely flowering habit with about eleven open and developing inflorescences per plant at one time.

*Inflorescence buds*.—Height: About 1.9 cm. Diameter: About 1.9 cm. Shape: Globular. Color: Close to 143A to 143B; towards the apex, close to 53C to 53D.

*Inflorescence size*.—Diameter: About 7.1 cm. Depth (height): About 2.9 cm. Diameter of disc: About 2.2 cm. Receptacle height: About 3 mm. Receptacle diameter: About 3 mm. Receptacle color: Close to 145D.

*Ray florets*.—Quantity and arrangement: About 50 per inflorescence arranged in about three whorls. Orientation: About 80° from vertical. Length: About 3.3 cm. Width: About 7.5 mm. Shape: Oblanceolate. Apex: Obtuse to abruptly acute. Base: Cuneate. Margin: Entire. Texture, upper surface: Smooth, glabrous; moderately velvety. Texture, lower surface: Smooth, glabrous; slightly velvety; slightly longitudinally ridged. Color: When opening, upper surface: Close to 65D and N155C. When opening, lower surface: Close to 51B to 51C. Fully opened, upper surface: Close to 55D and 58C to 58D; color becoming closer to 54A to 54D with development. Fully opened, lower surface: Close to 53D; color becoming closer to 59D with development.

*Disc florets*.—Quantity and arrangement: About 200 massed at center of receptacle. Length: About 1.5 cm. Width: About 6 mm. Shape: Tubular. Apex: Acute; upper 25%, free. Base: Lower 75%, fused. Margin: Entire. Texture, upper and lower surfaces: Smooth, glabrous. Color, prior to opening: Apex: Close to 8C. Mid-section: Close to 16C. Base: Close to 4D. Color, when opening and fully opened: Apex: Close to 4D. Mid-section: Close to 4D. Base: Close to 4D.

*Pappus*.—Quantity of hairs per floret: About 50. Length: About 6 mm. Diameter: Less than 1 mm. Texture: Soft. Color: Close to 11D.

*Phyllaries*.—Quantity and arrangement: About 60 per inflorescence arranged in about three whorls. Length: About 1.6 cm. Width (at base): About 2 mm. Shape: Lanceolate. Apex: Narrowly acute. Base: Cuneate. Margin: Entire. Texture, upper surface: Smooth, glabrous. Texture, lower surface: Densely tomentose. Color, upper surface: Close to 143B. Color, lower surface: Close to 143A.

*Scapes*.—Length: About 34.2 cm. Diameter: About 6 mm; distally, about 4 mm. Angle: About 10° from vertical. Strength: Strong. Texture: Moderately tomentose. Color: Close to 144A to 144B; distally, close to 147C.

*Reproductive organs*.—Androecium (present on disc florets only): Quantity per floret: Five. Filament length: About 7 mm. Filament color: Close to 11D. Anther shape: Lanceolate. Anther length: About 4 mm. Anther color: Close to 12A to 12B. Pollen amount: Moderate. Pollen color: Close to 15A. Gynoecium (present only on ray florets): Quantity per floret: One. Pistil length: About 1.1 cm. Stigma shape: Cleft. Stigma color: Close to 8C. Style length: About 1.05 cm. Style color: Close to 11D. Ovary color: Close to 155A.

*Seeds and fruits*.—Seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance and to be relatively tolerant to wind and rain. Plants of the new *Gerbera* have been observed to tolerate high temperatures about 35° C. and to be cold hardy to USDA Hardiness Zone 6.

It is claimed:

1. A new and distinct *Gerbera* plant named 'Garjasmina Imp.' as illustrated and described.

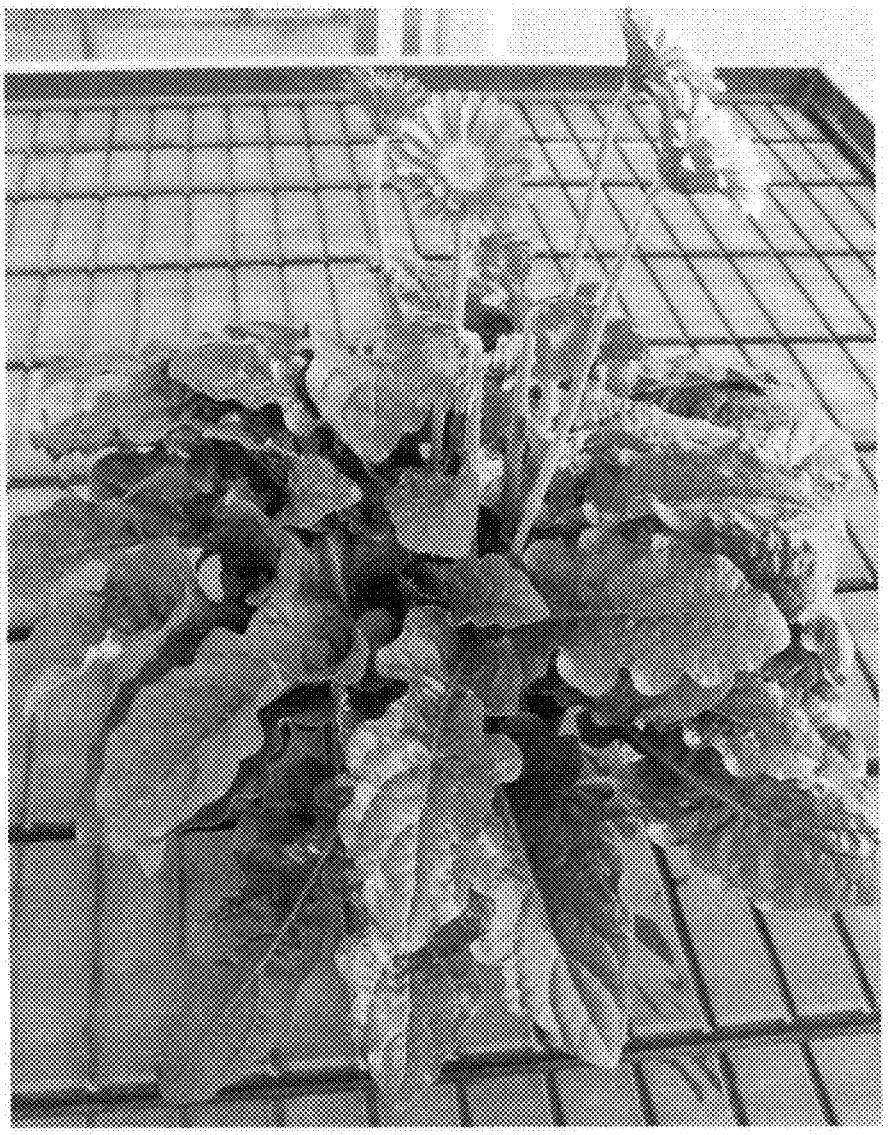

* * * * *